United States Patent [19]

Alster

[11] Patent Number: 4,990,631

[45] Date of Patent: Feb. 5, 1991

[54] PROCESS FOR THE PREPARATION OF 2,2-DIALKOXY CYCLIC ORTHO ESTERS DERIVED FROM LACTONES

[75] Inventor: Karol Alster, Farum, Denmark

[73] Assignee: Alza Corporation, Palo Alto, Calif.

[21] Appl. No.: 530,759

[22] Filed: May 30, 1990

[51] Int. Cl.$^5$ .......................................... C07D 307/20
[52] U.S. Cl. .................................................. 549/476
[58] Field of Search .......................................... 549/476

[56] References Cited

PUBLICATIONS

Meerwein et al., Chem. Ber., 1956, 89:2060.
Borch, J. Org. Chem., 1969, 34:627.
Mir-Mohamad-Sadeghy et al., J. Org. Chem., 1983, 48:2237.
Cornejo et al., J. Org. Chem., 1983, 48:3869.
Pollart et al., J. Org. Chem., 1986, 51:3155.
Mock et al., J. Org. Chem., 1981, 46:2557.

Primary Examiner—Richard L. Raymond
Attorney, Agent, or Firm—Jacqueline S. Larson; Edward L. Mandrell; Steven F. Stone

[57] ABSTRACT

This invention is directed to a process for the synthesis of 2,2-dialkoxy cyclic ortho esters derived from lactones which comprises reacting trialkyl orthoformate with boron trifluoride to give dialkoxymethylium tetrafluoroborate; reacting dialkoxymethylium tetrafluoroborate with a lactone to give the corresponding O-alkyllactonium tetrafluoroborate; and reacting the O-alkyllactonium tetrafluoroborate with an alkoxide, or alternatively with an alkanol in the presence of a base; wherein the first two steps of the process of the invention are conducted in the absence of solvents, other than the reactants themselves. The third step may also optionally be run without solvents.

The invention is also directed to the preparation of the O-alkyllactonium tetrafluoroborate in one reaction vessel; that is, the boron trifluoride is added to the trialkyl orthoformate and the lactone in a single reaction vessel. As the intermediate dialkoxymethylium tetrafluoroborate is formed, it reacts in situ with the lactone in the reaction mixture, thus avoiding the additional steps of separating the dialkoxymethylium tetrafluoroborate and then reacting it with the lactone in a separate step and vessel.

18 Claims, No Drawings

PROCESS FOR THE PREPARATION OF 2,2-DIALKOXY CYCLO ORTHO ESTERS DERIVED FROM LACTONES

FIELD OF THE INVENTION

This invention relates to the preparation of 2,2-dialkoxy cyclic ortho esters derived from lactones, and particularly to the preparation of 2,2-diethoxytetrahydrofuran.

BACKGROUND OF THE INVENTION

The synthesis of 2,2-diethoxytetrahydrofuran (DETHF) described in the literature (Meerwein et al., Chem. Ber., 1956, 89:2060) is the reaction of γ-butyrolactone with triethyloxonium tetrafluoroborate and the subsequent reaction of the resulting O-ethyllactonium tetrafluoroborate with sodium ethoxide. This synthesis produces ethyl ether as a byproduct; additionally, ethyl ether is required as a starting material in the manufacture of the triethyloxonium tetrafluoroborate. Thus, the process is not suitable for large-scale production because it involves substantial quantities of ethyl ether, which is low-boiling and inflammable. Furthermore, the process is unsuitable because of the presence of unstable, hygroscopic intermediates and because of the many time consuming operations required to be carried out in the process, such as isolation of the various intermediates.

An alternative method for preparing cyclic ortho esters derived from related lactones has been discussed by several researchers. See, Mir-Mohamad-Sadeghy et al., J. Org. Chem., 1983, 48:2237; Cornejo et al., J. Org. Chem., 1983, 48:3869; Pollart et al., J. Org. Chem., 1986, 51:3155. Following this method, a lactone is reacted with a dialkoxymethylium tetrafluoroborate to give the O-alkyllactonium tetrafluoroborate intermediate, which is then reacted with sodium ethoxide as in Meerwein (supra). However, the same drawbacks attend this procedure, namely: dialkoxymethylium tetrafluoroborate is prepared using boron trifluoride etherate as a starting material as well as ether and methylene chloride as solvents (Borch, J. Org. Chem., 1969, 34:627), other solvents such as methylene chloride and carbon tetrachloride are used throughout the process, and at each step intermediates are isolated prior to the next synthetic step.

It is therefore desirable to find an alternative method of synthesizing 2,2-dialkoxy cyclic ortho esters derived from lactones, such as 2,2-diethoxytetrahydrofuran, without the use of solvents, and in particular of ether. It is also desirable to find a synthetic process which avoids isolation of intermediates.

SUMMARY OF THE INVENTION

This invention is directed to a process for the synthesis of 2,2-dialkoxy cyclic ortho esters derived from lactones which comprises reacting trialkyl orthoformate with boron trifluoride to give dialkoxymethylium tetrafluoroborate; reacting dialkoxymethylium tetrafluoroborate with a lactone to give the corresponding O-alkyllactonium tetrafluoroborate; and reacting the O-alkyllactonium tetrafluoroborate with an alkoxide, or alternatively with an alkanol in the presence of a base; wherein the first two steps of the process of the invention are conducted in the absence of solvents, other than the reactants themselves. The third step may also optionally be run without solvents.

The invention is also directed to the preparation of the O-alkyllactonium tetrafluoroborate in one reaction vessel; that is, the trialkyl orthoformate, lactone and boron trifluoride are all placed together in a single reaction vessel. As the intermediate dialkoxymethylium tetrafluoroborate is formed, it reacts in situ with the lactone in the reaction mixture, thus avoiding the additional steps of separating the dialkoxymethylium tetrafluoroborate and then reacting it with the lactone in a separate step and vessel.

DETAILED DESCRIPTION OF THE INVENTION

The process of the present invention for the synthesis of a preferred embodiment, 2,2-diethoxytetrahydrofuran (I), is outlined below.

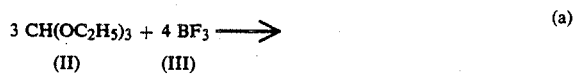

(a)

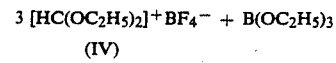

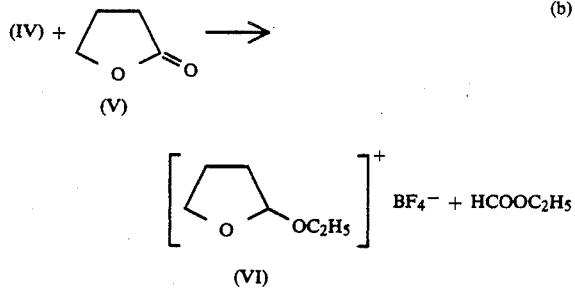

(b)

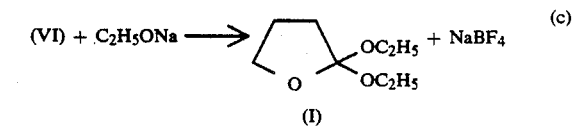

(c)

In the above synthesis, boron trifluoride (III) is bubbled into triethyl orthoformate (II) under a nitrogen atmosphere and at a temperature below 0° C., such as −30° C. The resulting compound diethoxymethylium tetrafluoroborate (IV) then reacts with γ-butyrolactone (V), at a temperature below 0° C., to give O-ethyl-γ-butyrolactonium tetrafluoroborate (VI). Compound (VI) is reacted with sodium ethoxide in the presence of a solvent such as ethanol and/or methylene chloride, and at a temperature below room temperature such as 0° C. to give the final product 2,2-diethoxytetrahydrofuran (I). Alternatively, ethanol in the presence of a base such as triethylamine or ammonia may be used in place of the sodium ethoxide in step (c), without the need of a solvent.

It is to be understood that while the above outlined synthesis is directed to the preparation of a preferred embodiment, the synthetic route is equally applicable to the preparation of 2,2-dialkoxy cyclic ortho esters derived from lactones generally.

As used herein, the term "alkoxy" refers to a lower alkoxy group of 1 to 6 carbon atoms, straight or branched, and preferably of 1 to 4 carbon atoms, more preferably methyl or ethyl. It is also preferred that the group be a primary alkoxy group. Thus, for example, dimethoxymethylium tetrafluoroborate, di-n-propoxymethylium tetrafluoroborate and di-n-butoxymethylium tetrafluoroborate may be prepared from trimethyl orthoformate, tri-n-propyl orthoformate and tri-n-butyl orthoformate, respectively, and boron trifluoride.

Many lactones may be used in place of γ-butyrolactone in the synthetic reaction, such as, for example, δ-valerolactone, 1(3H)isobenzofuranone, 1(3H)-benzo[e]isobenzofuranone, 3(1H)-benzo[e]isobenzofuranone, 1(3H)-benzo[f]isobenzofuranone and 3(1H)-benzo[f]isobenzofuranone. The lactone may be substituted, such as 4-methyl-γ-butyrolactone, 5-methyl-γ-butyrolactone, 5-ethyl-γ-butyrolactone and 5,5-dimethyl-γ-butyrolactone. Preferably, the lactones are chosen from those that are liquid at the reaction temperature. However, if a lactone is crystalline at reaction temperature, an excess of the trialkyl orthoformate may be used as a solvent.

Surprisingly, it has now been found that synthetic step (a) can be run without the presence of ether in the reaction. This is unexpected in view of the prior references which teach that ether is required. Additionally, it has also now been found that steps (a) and (b), and optionally step (c), do not require the addition of any solvent other than the reactants themselves.

It has also been found that the above synthesis may be carried out without isolating the dialkoxymethylium tetrafluoroborate prior to its reaction with the lactone. Thus, in a preferred embodiment, steps (a) and (b) of the process are combined and carried out in a single reaction vessel. Boron trifluoride (III) is added to a mixture of compounds (II) and (V) in one reaction vessel at the beginning of the procedure, and intermediate (IV) is not isolated from the reaction mixture but rather reacts as formed with compound (V) in situ. This is desirable in that it eliminates the timeconsuming step of isolating the intermediate and in that less equipment is required.

The 2,2-dialkoxy cyclic ortho esters produced by the reaction of the present invention can be recovered from the reaction mixture by conventional techniques. Examples of such techniques are solvent extraction and distillation.

The process of the present invention gives final product in good yield and without use of unsafe or otherwise undesirable solvents and without unstable intermediates. Additionally, the final product is easily separated from any side products, and the side products do not affect the yields of the final product.

The reactants are generally used in approximately stoichiometric proportions. Any of the reactants, other than boron trifluoride, may be used in excess.

In particular, an excess of the lactone may be used and is preferred, the excess functioning as a solvent for the reaction system. Alternatively, an excess of the trialkyl orthoformate may be used as a solvent. Steps (a) and (b) are otherwise run without solvents. The excess lactone or orthoformate remaining in the system at the end of the reaction may be separated and recycled.

When an alkanol is present in a stoichiometric amount as a reactant in step (c), addition of a solvent is not necessary.

The following examples are offered to illustrate the practice of the present invention and are not intended to limit the invention in any manner.

EXAMPLE I

A. A dry, 250-ml reaction flask was charged with triethyl orthoformate (87.3 g, 0.59 mol) and γ-butyrolactone (86 g, 1.0 mol) under a nitrogen atmosphere. The resulting solution was cooled to −30° C. with stirring, and boron trifluoride (50.5 g, 0.74 mol) was bubbled into the stirred mixture at a controlled rate, while the temperature was maintained at −30° C. The reaction mixture was then heated to 18° C. and stirred at 18-22° C. for two hours, and the resulting emulsion was then cooled to −5° C.

B. A 500-ml reaction flask was charged with sodium ethoxide (47.6 g, 0.70 mol) and ethanol (300 ml). The reaction mixture from procedure A was placed into a dropping funnel, and the two phases were allowed to separate. The dark-red bottom phase was added dropwise to the vigorously stirred solution of sodium ethoxide at 0° C. over 30–40 min. The resulting white suspension was stirred at 0° C. for 1 hour and then poured into a solution of sodium hydrogen carbonate in water at 5-10° C. The resulting emulsion was extracted with methylene chloride. The methylene chloride solution was dried over potassium carbonate, filtered and concentrated under vacuum. The remaining oil was purified by distillation to give 2,2-diethoxytetrahydrofuran (61.3 g, 69%) as a colorless liquid, b.p. 56.0–57.5° C., $n_D^{25}$ 1.4181.

Found C 60.1 H 10.1

Calculated for $C_8H_{16}O_3$ (160.2) C 60.0 H 10.1

EXAMPLE II

The reaction mixture from procedure A in Example I was poured into a mixture of ethanol (50 ml) and triethylamine (72 ml). The product was isolated similarly to the procedure in Example I to give 2,2-diethoxytetrahydrofuran in 64% yield.

EXAMPLE III

A. A flask was charged with γ-butyrolactone (21 kg, 244 mol) and triethyl orthoformate (27 kg, 182 mol), and the clear solution was stirred and cooled to −18° C. Boron trifluoride (16 kg, 236 mol) was bubbled into the reaction mixture over 3 hours while keeping the reaction temperature at −15 to −18° C. The resulting emulsion was warmed to 20° C. over half an hour and kept at 20° C. for 2 hours. The emulsion was then cooled and kept at −10° C. overnight with slow stirring.

B. A glass-lined reactor was charged with methylene chloride (50 l). Sodium ethoxide (17 kg, 250 mol) was added with stirring, and the resulting suspension was cooled to 0° C.

The emulsion from procedure A was allowed to separate, and the lower phase was added to the suspension of procedure B with efficient stirring, while the temperature was kept at 0° C. The product was isolated from the suspension as in Example I to give 2,2-diethoxytetrahydrofuran.

What is claimed is:

1. A process for the preparation of 2,2-di-$C_{1-6}$alkoxy cyclic ortho esters derived from lactones which comprises:
   (a) reacting tri-$C_{1-6}$alkyl orthoformate with boron trifluoride to give di-$C_{1-6}$alkoxymethylium tetrafluoroborate;
   (b) reacting di-$C_{1-6}$alkoxymethylium tetrafluoroborate with a lactone to give O-$C_{1-6}$alkyllactonium tetrafluoroborate; and (c) reacting O-$C_{1-6}$alkyllactonium tetrafluoroborate with $C_{1-6}$alkoxide, or with $C_{1-6}$alkanol and a base to give the 2,2-di-$C_{1-6}$alkoxy cyclic ortho ester;

wherein, steps (a) and (b) are conducted in the absence of solvents, other than the reactants themselves.

2. A process according to claim 1 wherein the lactone is present in an excess amount.

3. A process according to claim 1 wherein the tri-$C_{1-6}$alkyl orthoformate is present in an excess amount.

4. A process according to claim 1 wherein steps (a) and (b) are carried out in a single reaction vessel.

5. A process according to claim 2 wherein steps (a) and (b) are carried out in a single reaction vessel.

6. A process according to claim 3 wherein steps (a) and (b) are carried out in a single reaction vessel.

7. A process according to claim 1 wherein the base is triethylamine or ammonia.

8. A process for the preparation of 2,2-diethoxytetrahydrofuran which comprises:
 (a) reacting triethyl orthoformate with boron trifluoride to give diethoxymethylium tetrafluoroborate;
 (b) reacting diethoxymethylium tetrafluoroborate with γ-butyrolactone to give O-ethyl-γ-butyrolactonium tetrafluoroborate; and
 (c) reacting O-ethyl-γ-butyrolactonium tetrafluoroborate with ethoxide, or with ethanol and a base to give 2,2-diethoxytetrahydrofuran;

wherein, steps (a) and (b) are conducted in the absence of solvents, other than the reactants themselves.

9. A process according to claim 8 wherein the γ-butyrolactone is present in an excess amount.

10. A process according to claim 8 wherein the triethyl orthoformate is present in an excess amount.

11. A process according to claim 8 wherein steps (a) and (b) are carried out in a single reaction vessel.

12. A process according to claim 9 wherein steps (a) and (b) are carried out in a single reaction vessel.

13. A process according to claim 10 wherein steps (a) and (b) are carried out in a single reaction vessel.

14. A process according to claim 8 wherein the base is triethylamine or ammonia.

15. A process for the preparation of 2,2-diethoxytetrahydrofuran which comprises:
 (a) adding boron trifluoride to triethyl orthoformat and γ-butyrolactone to give O-ethyl-γ-butyrolactonium tetrafluoroborate; and
 (b) reacting O-ethyl-γ-butyrolactonium tetrafluoroborate with ethoxide, or with ethanol and a base to give 2,2-diethoxytetrahydrofuran; wherein, step (a) is conducted in the absence of solvents, other than the reactants themselves.

16. A process according to claim 15 wherein the γ-butyrolactone is present in an excess amount.

17. A process according to claim 15 wherein the triethyl orthoformate is present in an excess amount.

18. A process according to claim 15 wherein the base is triethylamine or ammonia.

* * * * *

UNITED STATES PATENT AND TRADEMARK OFFICE
CERTIFICATE OF CORRECTION

PATENT NO. : 4,990,631
DATED : February 5, 1991
INVENTOR(S) : Karol Alster

It is certified that error appears in the above-identified patent and that said Letters Patent is hereby corrected as shown below:

Column 6, line 15, "orthoformat" should read --orthoformate--.

Signed and Sealed this

Nineteenth Day of May, 1992

*Attest:*

DOUGLAS B. COMER

*Attesting Officer*  Acting Commissioner of Patents and Trademarks